(12) United States Patent
Yang et al.

(10) Patent No.: US 6,297,879 B1
(45) Date of Patent: *Oct. 2, 2001

(54) INSPECTION METHOD AND APPARATUS FOR DETECTING DEFECTS ON PHOTOMASKS

(75) Inventors: Baorui Yang; Christophe Pierrat, both of Boise, ID (US)

(73) Assignee: Micron Technology, Inc., Boise, ID (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,100

(22) Filed: Feb. 27, 1998

(51) Int. Cl.⁷ .................................................. G01N 21/00
(52) U.S. Cl. ........................ 356/237.5; 356/394; 382/144
(58) Field of Search .................................. 356/394, 390, 356/237.5, 392, 398, 237.1, 237.2, 237.4; 382/144, 218; 348/126

(56) References Cited

U.S. PATENT DOCUMENTS

| | | | |
|---|---|---|---|
| 3,909,602 | * | 9/1975 | Micka .................................. 356/237.5 |
| 4,628,531 | * | 12/1986 | Okamoto et al. .................. 356/237.5 |
| 4,641,353 | * | 2/1987 | Kobayashi ............................... 382/8 |
| 4,659,220 | * | 4/1987 | Bronte et al. ...................... 356/237.5 |
| 5,038,048 | * | 8/1991 | Maeda et al. .................... 250/559.41 |
| 5,790,247 | * | 8/1998 | Henley et al. ....................... 356/237 |

OTHER PUBLICATIONS

Schwart, J., "Process and Machine Mastering Employing WF–710 Wafer Inspection System", Metrology, Inspection, and Process Control for Microlithography X, Santa Clara, CA: SPIE Proceedings Series, vol. 2725, 242–54, (Mar. 11–13, 1996).

* cited by examiner

Primary Examiner—Hoa Q. Pham
(74) Attorney, Agent, or Firm—Schwegman, Lundberg, Woessner & Kluth, P.A.

(57) ABSTRACT

A method of photomask inspection uses available technology in a novel fashion to detect defects on a photomask. The method involves inspecting a photomask using a modified microscope, image comparison software, and a CCD camera. The microscope is modified to view the photomask out of focus and at low magnifications. The photomask may be scanned at multiple focuses to implement the inspection. This image is then compared with a reference image, such as an image from another die or a database. Any discrepancies between the images indicate a defect in the photomask. Alternatively, the photomask is inspected using a low magnification, low NA objective in dark field image of the optical microscope.

41 Claims, 6 Drawing Sheets

INSPECTION METHOD AND APPARATUS FOR DETECTING DEFECTS ON PHOTOMASKS

FIELD OF THE INVENTION

The present invention generally relates to the manufacture of semiconductor devices. In particular, the present invention relates to inspection techniques used for detecting defects on photomasks used in photolithography.

BACKGROUND OF THE INVENTION

The capacity of integrated circuits has increased primarily as the result of reductions in the size of features on a semiconductor chip. The lateral dimensions of features are generally defined by photolithographic techniques in which a detailed pattern is transferred to a reactive material by shining light through a photomask or reticle. During the photolithography process, energy is applied to photo resist deposited on a wafer, where the energy application is controlled through the use of a patterned photomask. The exposure to the wafer is made by a step and repeat procedure. In this procedure, the wafer is moved and the steppers are used to move and repeat the pattern of the photomask over the wafer. Since accuracy of the pattern is essential as it is repeated several times, the pattern of the photomask is enlarged when it is created and reduced while it is being exposed on the wafer. Although some defects are effectively eliminated by the use of a $1/10$ or a $1/5$ reduction stepper, many defects remain as minimum feature size on the photomask continues to decrease. Moreover, the decrease in minimum feature size has increased the printability of certain types of defects because a slight variation of the exposure dose can cause repeating defects on the wafer.

Printable defects on photomasks and reticles have historically been a source of defects that have reduced die yields. Printable defects in the photomasks are repeated many times over the surface of a semiconductor wafer since the photomask is stepped and repeated over the wafer. For fatal defects, this can result in substantial yield losses. Accordingly, it is important to detect and correct as many defects as possible in the photomasks.

Since fatal defects in a mask or reticle are highly undesirable, it would be useful if such defects could be repaired, thereby rendering the mask free of fatal defects. One of the mask repair methods for accomplishing this purpose is laser repair of the photomask. After the defect has been corrected by the laser repair, the photomask must be inspected again to verify the repair. However, defects which continue to exist after laser repair can also remain undetected and continue to print on the wafer. Therefore, inspection of photomasks is an important step in the photolithography process.

Originally, photomasks and wafers were inspected manually with a microscope. Manual optical inspection enabled identification of a wide range of defect types on a variety of process steps but was extremely slow and strongly dependent on the operator. Manual inspection evolved into automatic inspection employing high resolution CCD imaging system performing image capturing on two similar pattern zones and image comparison.

Other approaches to inspecting photomasks include U.S. Pat. No. 4,641,353 to Kobayashi on Feb. 3, 1987, which teaches projecting an optical image of a photomask pattern on to an image sensor. The image sensor converts the image and compares it to design data. The inspection is done just prior to the process of exposing the mask pattern on the wafer.

Conventional inspection methods, however, have difficulties in detecting all potential defects. The current mask defect inspection systems, such as KLA 351, Orbot RT-8000, and Lasertec normally consist of a high magnification and high resolution imaging system, and the photomask is scanned pixel by pixel. However, even when passing incoming inspection using these types of inspection techniques, certain types of defects were continuing to print on the wafer. Locating these types of defects then involves the time consuming process of finding the defect on the wafer to determine where the defect on the mask is located.

Other particle inspection systems, such as QCO and Horiba, rely on the detection of the scattered light from the defect. The particle inspection systems are not sensitive to certain defects, such as cleaning stains or local resist misprocessing. These defects do not scatter enough light to be detected by these inspection systems. Thus, the defects are undetected by these inspection systems.

After the automatic inspection of the photomasks, the operator has to evaluate all the defects found by the automatic inspection and classify whether the defect is false or real. The current inspection systems are capable of finding some defects, such as local small CD variation, shown in FIG. 1 or a stripe butting error (not shown). However, when an operator views the image in FIG. 2, the mask is inaccurately flagged defect-free since the defect is not readily apparent to humans. As a result, the defect is undetected and will print on the wafer during the photolithography process.

Certain defects remain undetected by conventional inspection methods, or are inaccurately flagged as defect-free. Thus, what is needed is an improved method of mask inspection process for detecting printable defects which are difficult to accurately detect using current inspection techniques.

SUMMARY OF THE INVENTION

One aspect of the present invention is to provide a method of photomask inspection which uses available technology in a novel fashion to detect defects on a photomask. Although this invention may detect other types of defects, the invention is particularly useful for inspecting for printable defects including local small CD variation, stripe batting error caused by the e-beam writing tool, cleaning stains, local resist misprocessing, clear extension, chrome extension, repairs, and other defects.

In one embodiment, a photomask is inspected using a modified microscope, image comparison software, and a CCD camera. The CCD camera captures an image of the photomask out of focus at a low magnification on the microscope. A reference image is generated, such as from another die or from a database containing original design data. The image of the photomask is then compared to the reference image by the image comparison software.

In another embodiment, the mask is scanned at multiple focuses to implement the inspection effectively. This image is then compared with a reference image, such as an image from another die or a database. Any discrepancies between the images indicate a defect in the photomask. In yet another embodiment, a photomask is inspected using an optical microscope at low magnification in a dark field mode, and compared to a reference image.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope of the present invention is defined by the appended claims.

Figure 1:
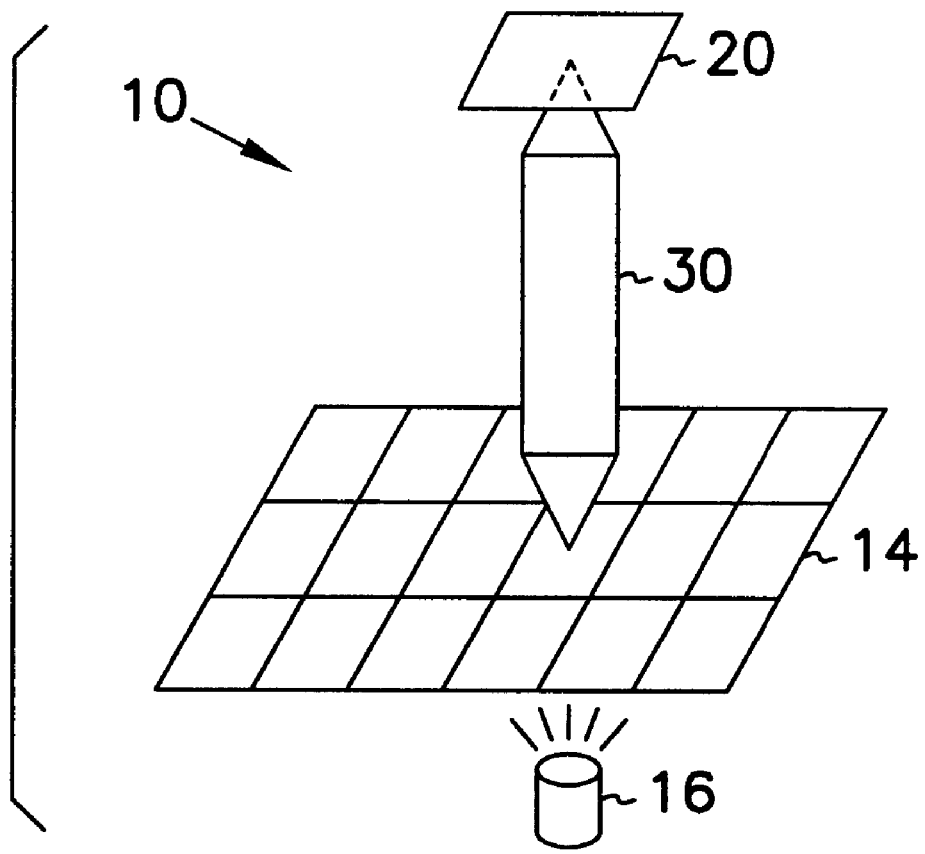
FIG. 1 illustrates a prior art inspection system.

A conventional inspection system 10 is shown in FIG. 1. Current mask defect inspection systems include KLA 351, Orbot RT-8000, and Lasertec. Illuminated by a light source 16, an image of the photomask 14 is generated by an optical microscope 30 at high magnification and high resolution, where the image appears in focus. The image of the photomask is then captured by a CCD image capture system 20. At the high resolution and high magnification, the CCD image capture system 20 scans the photomask 14 pixel-by-pixel. The images are automatically compared to either another die on the photomask, or an image generated from the database. One image is subtracted from the other, and a remaining difference indicates the presence of a defect and the die is flagged as having a defect.

After the mask is automatically inspected and flagged, an operator then manually checks the images to classify the defects, and to determine if the defect is false or real. Certain types of defects are not visible to an operator's eye at high resolutions and high magnifications.

Figure 2:
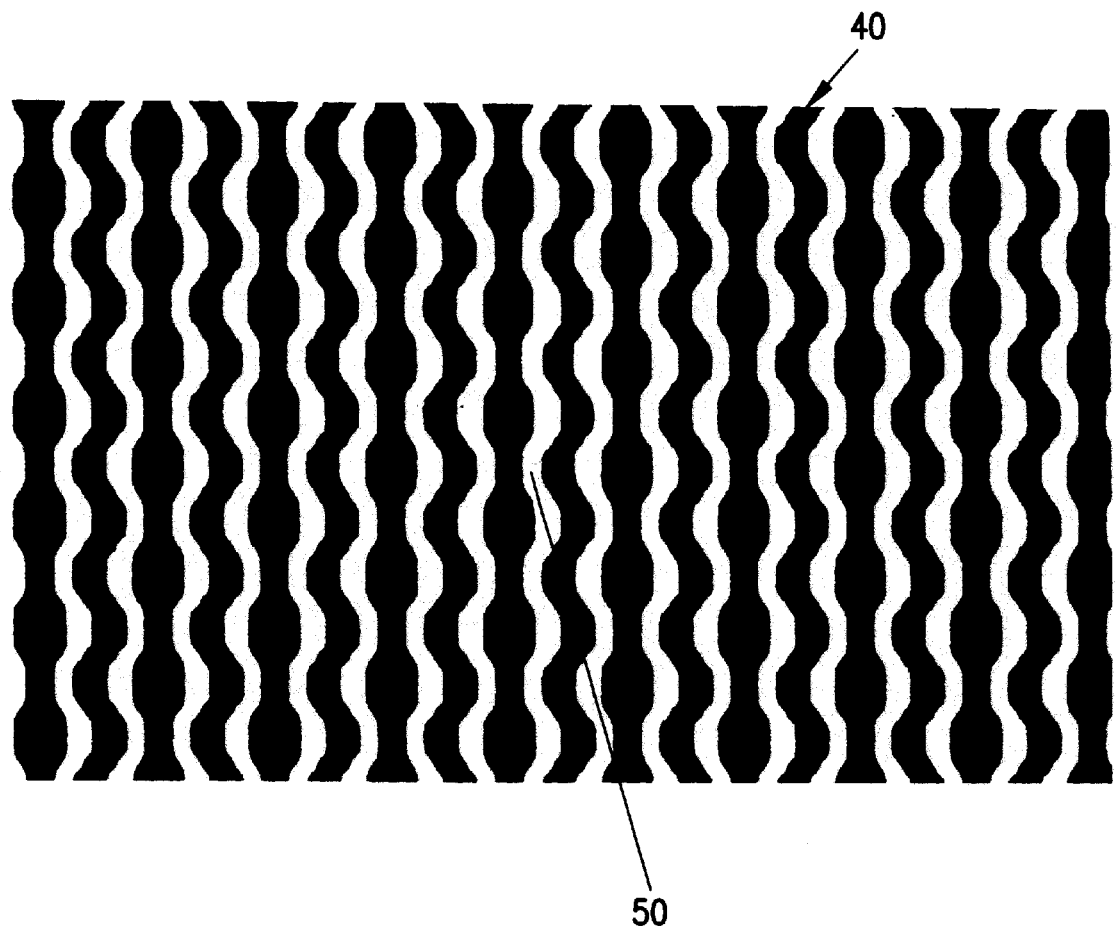
FIG. 2 illustrates an image of a defected mask obtained with a prior art inspection system as shown in FIG. 1, using prior art mask inspection techniques.

For example, FIG. 2 shows an image taken of a defected photomask 40 with the inspection system 10 of FIG. 1. The inspection system 10 may have a capability to find the CD variation defect, located in the center of FIG. 2, using an algorithm to measure the CD variation. The system 10 may also indicate where the defect is located, and brings the image on the screen. However, when the operator views the image shown in FIG. 2 during the classification process, the operator incorrectly classifies the defect 50 as false as the defect is not clearly visible to the operator.

Therefore, even though the current inspections systems mentioned above have the capability of high resolution CD measurement and can detect defects such as small CD variation, these defects will normally appear as false detection for human eyes. Other defects, such as cleaning stains or local resist misprocessing, normally do not provide sufficient contrast for human detection when using an autofocus imaging system at high magnifications. Furthermore, this type of inspection system has low throughput as the masks are inspected pixel-by-pixel.

Figure 3:
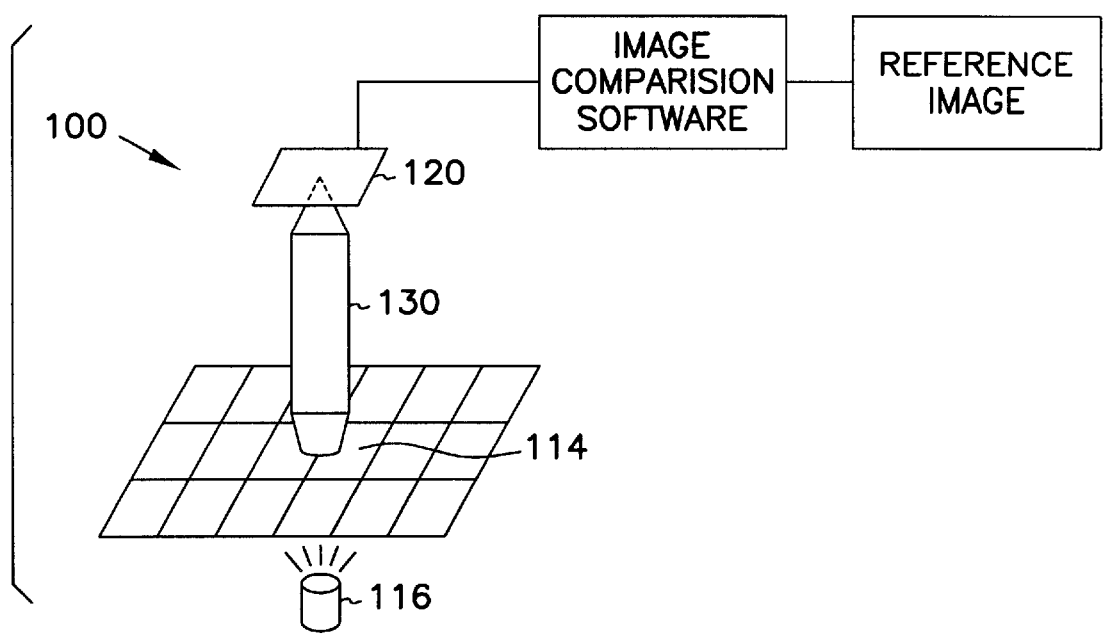
FIG. 3 illustrates an apparatus built in accordance with one embodiment of the present invention.

One embodiment of the present invention is shown in FIG. 3. An inspection system 100 is provided with an optical microscope 130 for generating an image of the photomask 114 and a CCD camera 120 for capturing the image. A light source 116 illuminates the photomask 114 and the image is acquired using an optical microscope 130 under optimized conditions. The acquisition conditions for the optical microscope are optimized by varying the sharpness of the image at low magnifications. As known by those skilled in the art, low magnifications can range from 1× to 500×.

Figure 4:
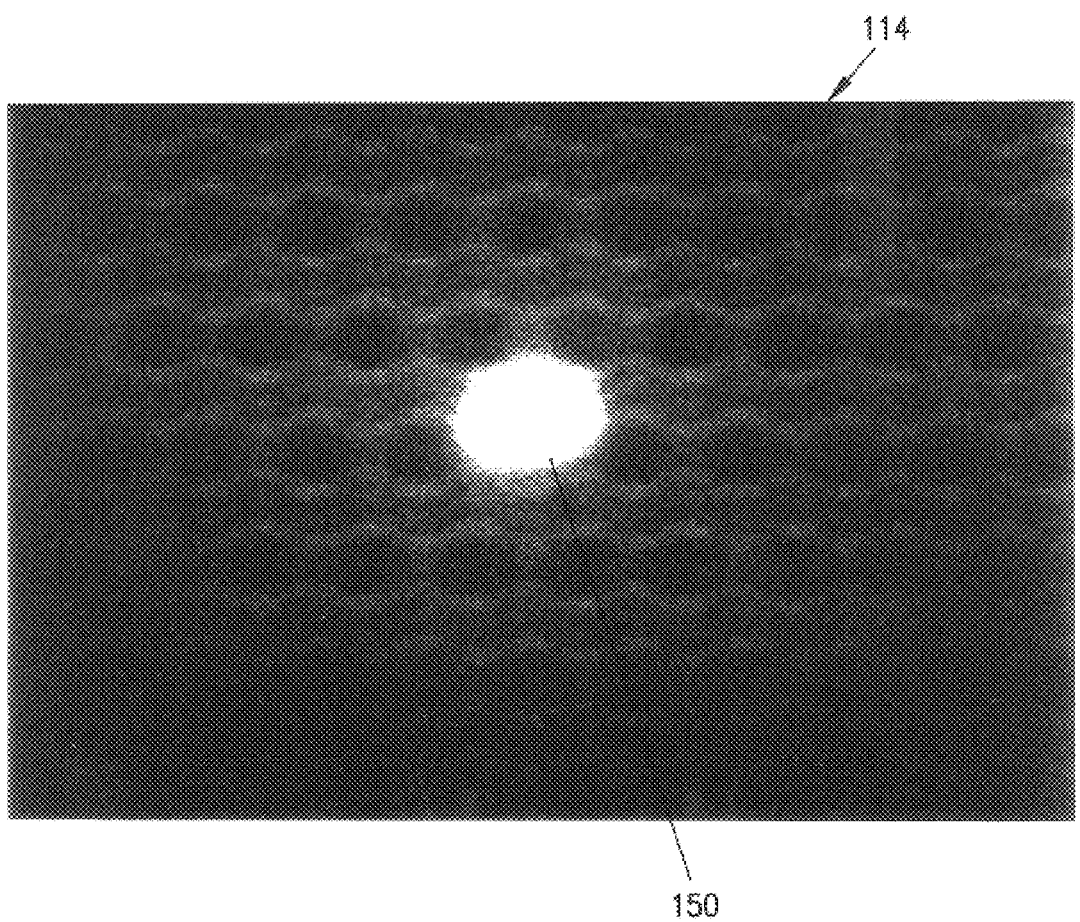
FIG. 4 illustrates an image of a defected mask obtained with the method of another embodiment of the invention.

To optimize the inspection process, the objective of the optical microscope is manipulated such that the image is viewed out of focus. Multiple scans conducted at varying levels of resolution may be required to fully optimize the defect viewing capabilities of the optical microscope 130. As generated by the inspection system 100 of FIG. 3, a captured image of the CD variation defect 150 is shown in FIG. 4. The captured image now clearly indicates where the defect 150 is on the photomask 114, and the operator can then correctly classify the defect 150 of the photomask 114.

The photomask is scanned area by area, instead of pixel by pixel scanning done by conventional systems. This allows for higher sensitivity to a defect that extends to a relatively larger area. Incorporating an automatic X-Y translation stage for manipulating the photomask to inspect the different areas within the photomask is within the scope of this invention.

Figure 5:
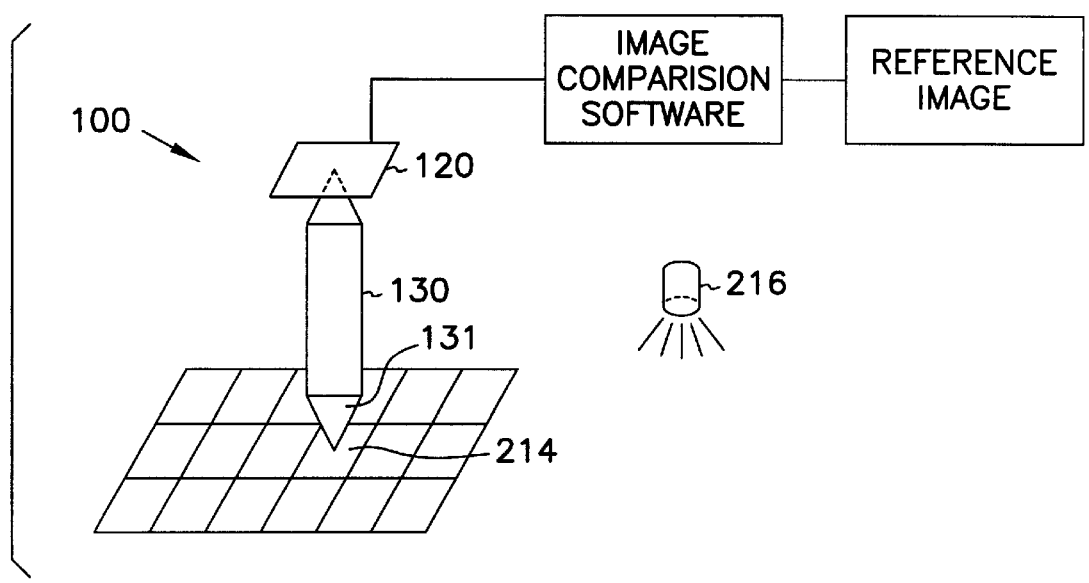
FIG. 5 illustrates an apparatus built in accordance with yet another embodiment of the present invention.
Figure 6:
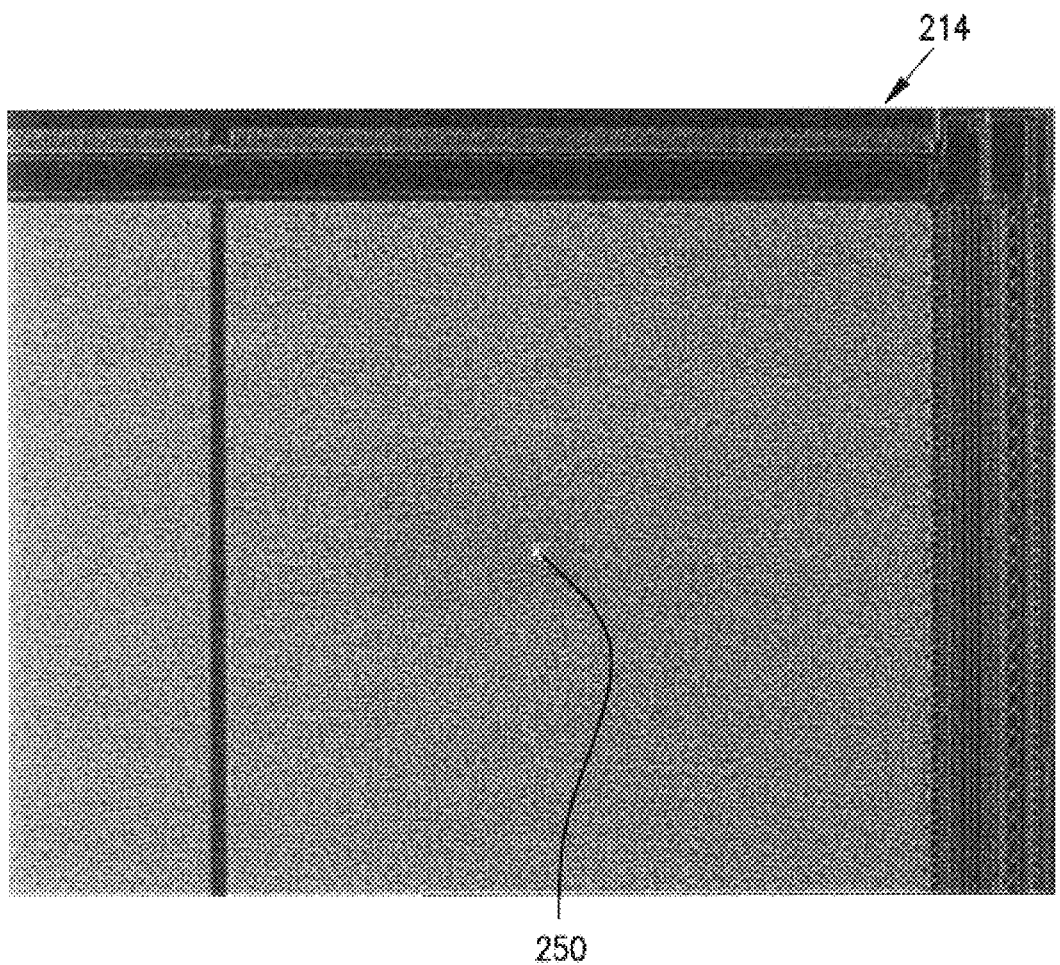
FIG. 6 illustrates an image of a defected mask obtained with the method of another embodiment of the invention.

Another embodiment of the present invention, shown in FIG. 5, includes using an optical microscope 130 in a dark field mode to detect defects on a photomask. A light source 216 is provided outside of the cone 131 encompassed by the objective. The light from the light source 216 strikes the photomask 214 obliquely, and the defects appears as a bright spot on the image. The image is captured at a low magnification and low NA, and compared with a similarly collected reference image. Although other low magnifications are within the scope of this invention, the image of the photomask shown in FIG. 6 was generated using a 5×objective and a NA equal to 0.13. As shown in FIG. 6, the photomask 214 appears as a black background, and the reflected defect 250 appears bright.

The present invention including all of the various embodiments, can be used in conjunction with, either a die-to-die comparison or a die-to-database comparison system, or other known image comparison systems. These types of comparison systems are well known in the art, and therefore, will not be further discussed.

Advantageously, the invention provides for high throughput, and an inexpensive technique for inspection of certain type of killing defects which cannot be detected with the current available mask inspection systems. The present invention allows a larger area of the photomask to be viewed, thereby making it easier to view the small defect. The inventive process simulates the conditions at which the mask prints on the wafer by viewing the mask at low magnifications, and enhances the printability of the defect when viewing the photomask out of focus. Several different types of defects car be detected with the present invention that are not normally detectable by present inspection systems, or are difficult to detect. Furthermore, the number of inaccurate classification of false defects are reduced.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of inspecting a photomask for defects, the method comprising the steps of:

generating a reference image of the photomask out of focus;

capturing said reference image of the photomask;

providing a photomask to be inspected;

generating an image of the photomask by scanning the photomask with an optical microscope set out of focus at low magnification, wherein said image is generated at less than 500×;

capturing said image of the photomask; and comparing said captured image of the photomask with the reference image to determine the presence of a defect therein.

2. The method as described in claim 1, wherein the step of generating the reference image includes generating the reference image from a reference die.

3. The method as described in claim 1, wherein step of generating the reference image includes generating the reference image from a database containing original pattern data of the photomask.

4. The method as described in claim 1, wherein step of comparing the captured image of the photomask with the reference image is done by an operator.

5. The method as described in claim 1, wherein the step of comparing the captured image of the photomask with the reference image is done by a software image comparison system.

6. The method as described in claim 1, wherein the step of generating an image of the photomask includes conducting a defocus scan, the defocus scan varies the resolution of the image captured by the optical microscope, whereby the image of the defect is optimized.

7. The method as described in claim 1, wherein the step of capturing the image of the photomask includes capturing the image using a CCD camera.

8. The method as described in claim 7, wherein said mask was corrected by a laser.

9. The method as described in claim 1, wherein said mask has been repaired from defects discovered in an earlier inspection.

10. A method of inspecting a photomask for defects, the method comprising:

generating an out-of-focus reference image at low magnification;

capturing said out-of-focus reference image;

providing a photomask to be inspected;

generating an out-of-focus image of the photomask by scanning the photomask with an optical microscope in dark field mode at low magnification, wherein said out-of-focus image is generated at less than 500×;

capturing said out-of-focus image of the photomask; and comparing said captured out-of-focus image of the photomask with the out-of-focus reference image to determine the presence of a defect therein.

11. The method of inspecting a photomask for defects according to claim 10, wherein generating a reference image includes generating the reference image from a reference die.

12. The method of inspecting a photomask for defects according to claim 11, wherein generating a reference image includes generating the reference image from a database containing design information of the photomask.

13. An apparatus for detecting defects in photomasks, the apparatus comprising:

an optical microscope, said microscope modified to scan images of the photomask out of focus at low magnification, said microscope including an objective of less than 500×;

a CCD camera coupled to the optical microscope for capturing the scanned out-of-focus images of the photomask;

a database containing original design data for generating an out-of-focus reference image; and an image software comparison system coupled to the CCD camera and the database for comparing the captured out-of-focus image of the photomask with the generated out-of-focus reference image.

14. The apparatus for detecting defects in photomasks according to claim 13, wherein said optical microscope uses bright field imaging.

15. An apparatus for detecting defects in photomasks, the apparatus comprising:

an optical microscope set in dark field mode for scanning images of the photomask at low magnification, said microscope including an objective of less than 500×;

a CCD camera coupled to the optical microscope for capturing the out-of-focus scanned images of the photomask;

a database containing original design data for generating an out-of-focus reference image; and an image software comparison system coupled to the CCD camera and the database for comparing the out-of-focus captured image of the photomask with the generated out-of-focus reference image.

16. A method of inspecting a photomask for defects, the method comprising:

generating a reference image of the photomask out of focus;

capturing said out of focus reference image of the photomask;

providing a photomask to be inspected, the photomask having a pattern thereon;

generating an out of focus image of the photomask at low magnification, wherein said image is generated at less than 500×;

capturing said image of the photomask; and identifying whether a photomask defect is present including comparing said captured image of the photomask with the reference image to determine the presence of a defect therein.

17. The method as recited in claim 16, wherein generating the out of focus image of the photomask includes scanning the photomask with an optical microscope set out of focus at low magnification.

18. The method as recited in claim 16, wherein generating the out of focus image of the photomask includes modifying an objective of an optical microscope.

19. The method as recited in claim 16, wherein generating the out of focus reference image includes generating the reference image from a reference die.

20. The method as recited in claim 16, further comprising scanning an area of the photomask.

21. The method as recited in claim 16, further comprising modifying the magnification of the out of focus image and the out of focus reference image, and capturing the modified out of focus images.

22. The method as recited in claim 16, wherein comparing said captured image of the photomask with the reference image to determine the presence of a defect therein includes comparing the images at multiple different resolutions.

23. The method as recited in claim 16, wherein generating the out of focus image of the photomask at low magnification includes generating the out of focus image of the photomask at 5×.

24. The method as recited in claim 16, wherein generating the out of focus image of the photomask includes scanning the photomask with an optical microscope in dark field mode at low magnification.

25. The method as recited in claim 24, wherein comparing said captured image of the photomask with the reference image to determine the presence of a defect therein includes comparing the images at multiple different resolutions.

26. The method as recited in claim 16, further comprising directing light from a light source such that the light strikes the photomask obliquely.

27. A method of inspecting a photomask for defects, the method comprising:

generating an out of focus reference image of the photomask, including generating the out of focus reference image from a reference die;

capturing said out of focus reference image of the photomask;

providing a photomask to be inspected the photomask having a pattern thereon;

modifying an objective of an optical microscope;

scanning an area of the photomask with the optical microscope set out of focus;

generating an out of focus image of the photomask at low magnification, wherein said image is generated at less than 500×;

capturing said image of the photomask;

identifying whether a photomask defect is present including comparing said captured image of the photomask with the reference image to determine the presence of a defect therein; and modifying the magnification of the out of focus image and the out of focus reference image, and capturing the modified out of focus images.

28. The method as recited in claim 27, wherein generating the out of focus image of the photomask includes scanning the photomask with an optical microscope in dark field mode at low magnification.

29. An apparatus for detecting defects in photomasks, the apparatus comprising:

an optical microscope, said microscope modified to scan images of the photomask out of focus at low magnification of less than 500×, the photomask having a pattern thereon, the optical microscope including a light source;

a means for generating an out of focus reference image;

a means for capturing the out of focus images of the photomask; and a means for comparing the out of focus reference image with an out of focus image of the photomask, wherein the means for comparing comprises a means for determining whether the photomask has a defect.

30. The apparatus as recited in claim 29, wherein the means for generating an out of focus reference image includes a database containing original design data for generating an out of focus reference image.

31. The apparatus as recited in claim 30, further comprising an image software comparison system coupled to the means for capturing the out of focus images of the photomask and the database for comparing the captured image of the photomask with the generated reference image.

32. The apparatus as recited in claim 29, wherein the optical microscope is set to scan the photomask at 5×.

33. The apparatus as recited in claim 29, wherein the light source is disposed relative to the optical microscope such that the optical microscope scans the photomask in dark field mode.

34. The apparatus as recited in claim 33, wherein the captured image of the photomask has a dark background, and a reflected defect appears bright relative to the dark background.

35. An apparatus for detecting defects in photomasks, the apparatus comprising:

an optical microscope, said microscope modified to scan images of the photomask out of focus at low magnification of less than 500×, the photomask having a pattern thereon, the optical microscope including a light source, the light source is disposed relative to the optical microscope such that the optical microscope scans the photomask in dark field mode;

a means for generating an out of focus reference image;

a means for capturing the out of focus images of the photomask;

a means for comparing the out of focus reference image with an out of focus image of the photomask, wherein the means for comparing comprises a means for determining whether the photomask has a defect;

an image software comparison system coupled to the means for capturing the out of focus images of the photomask and the database for comparing the captured image of the photomask with the generated reference image; and wherein the captured image of the photomask has a dark background, and a reflected defect in the pattern of the photomask appears bright relative to the dark background.

36. A method of inspecting a photomask for defects, the method comprising:

generating a reference image of the photomask out of focus, capturing said out of focus reference image of the photomask;

providing a photomask to be inspected, the photomask having a pattern thereon;

generating an out of focus image of the photomask at low magnification, wherein said image is generated at less than 500×, and generating the out of focus image of the photomask includes modifying an objective of an optical microscope;

capturing said image of the photomask; and identifying whether a photomask defect is present including comparing said captured image of the photomask with the reference image to determine the presence of a defect therein.

37. A method of inspecting a photomask for defects, the method comprising:

generating a reference image of the photomask out of focus, capturing said out of focus reference image of the photomask;

providing a photomask to be inspected, the photomask having a pattern thereon;

generating out of focus image of the photomask at low magnification, wherein said image is generated at less than 500×;

capturing said out-of-focus image of the photomask; and identifying whether a photomask defect is present including comparing said out-of-focus captured image of the photomask with the out-of-focus reference image to determine the presence of a defect therein.

38. A method of inspecting a photomask for defects, the method comprising:

generating a reference image of the photomask out of focus, capturing said out of focus reference image of the photomask;

providing a photomask to be inspected, the photomask having a pattern thereon;

generating an out of focus image of the photomask at low magnification, wherein said image is generated at less than 500x;

capturing said image of the photomask;

identifying whether a photomask defect is present including comparing said captured image of the photomask with the reference image to determine the presence of a defect therein; and comparing said captured image of the photomask with the reference image to determine the presence of a defect therein includes comparing the images at multiple different resolutions.

39. A method of inspecting a photomask for defects, the method comprising:

generating a reference image of the photomask out of focus, capturing said out of focus reference image of the photomask;

providing a photomask to be inspected, the photomask having a pattern thereon;

generating an out of focus image of the photomask at low magnification, wherein said image is generated at less than 500x;

capturing said image of the photomask;

identifying whether a photomask defect is present including comparing said captured image of the photomask with the reference image to determine the presence of a defect therein; and generating the out of focus image of the photomask at low magnification includes generating the out of focus image of the photomask at 5x.

40. A method of inspecting a photomask for defects, the method comprising:

generating a reference image of the photomask out of focus, capturing said out of focus reference image of the photomask;

providing a photomask to be inspected, the photomask having a pattern thereon;

generating an out of focus image of the photomask at low magnification, wherein said image is generated at less than 500x;

capturing said image of the photomask;

identifying whether a photomask defect is present including comparing said captured image of the photomask with the reference image to determine the presence of a defect therein; and comparing said captured image of the photomask with the reference image to determine the presence of a defect therein includes comparing the images at multiple different resolutions.

41. An apparatus for detecting defects in photomasks, the apparatus comprising:

an optical microscope, said microscope modified to scan images of the photomask out of focus at low magnification of less than 500x, the photomask having a pattern thereon, the optical microscope including a light source;

a means for generating an out of focus reference image;

a means for capturing the out of focus images of the photomask;

a means for comparing the out of focus reference image with an out of focus image of the photomask, wherein the means for comparing comprises a means for determining whether the photomask has a defect; and the optical microscope is set to scan the photomask at 5x.

\* \* \* \* \*

UNITED STATES PATENT AND TRADEMARK OFFICE
CERTIFICATE OF CORRECTION

PATENT NO. : 6,297,879 B1
DATED : October 2, 2001
INVENTOR(S) : Yang et al.

It is certified that error appears in the above-identified patent and that said Letters Patent is hereby corrected as shown below:

<u>Column 2,</u>
Line 42, delete "batting" and insert -- butting --, therefor.

<u>Column 4,</u>
Line 35, delete "5×objective" and insert -- 5× objective --, therefor.
Line 54, delete "car" and insert -- can --, therefor.

<u>Column 6,</u>
Line 17, after "scanning" insert -- out of focus --.

<u>Column 8,</u>
Line 62, delete "generating out" and insert -- generating an out --, therefor.

Signed and Sealed this

Eleventh Day of June, 2002

Attest:

Attesting Officer

JAMES E. ROGAN
Director of the United States Patent and Trademark Office